United States Patent
Shimizu et al.

(10) Patent No.: US 7,242,542 B2
(45) Date of Patent: Jul. 10, 2007

(54) FILTERS OF ELECTRONIC DISPLAYS

(75) Inventors: Ikuo Shimizu, Yokkaichi (JP);
Motoharu Kinugasa, Yokkaichi (JP);
Hiroshi Toyoda, Yokkaichi (JP);
Masanori Ikuta, Yokkaichi (JP);
Kyoko Katagi, Inashiki-gun (JP)

(73) Assignee: Kyowa Hakko Chemical Co., Ltd., Tokyo (JP)

( * ) Notice: Subject to any disclaimer, the term of this patent is extended or adjusted under 35 U.S.C. 154(b) by 283 days.

(21) Appl. No.: 10/516,749

(22) PCT Filed: Jul. 3, 2003

(86) PCT No.: PCT/JP03/08479

§ 371 (c)(1),
(2), (4) Date: Dec. 6, 2004

(87) PCT Pub. No.: WO2004/005981

PCT Pub. Date: Jan. 15, 2004

(65) Prior Publication Data

US 2006/0063864 A1    Mar. 23, 2006

(30) Foreign Application Priority Data

Jul. 4, 2002    (JP) ............................. 2002-195456

(51) Int. Cl.
*G02B 5/22* (2006.01)
*C07D 209/02* (2006.01)

(52) U.S. Cl. ..................... 359/885; 428/1.31; 252/582; 252/586; 252/589

(58) Field of Classification Search ................. 428/1.3, 428/1.31; 252/582, 586, 589; 359/885; 568/670; 548/455
See application file for complete search history.

(56) References Cited

U.S. PATENT DOCUMENTS 6,596,364 B2 * 7/2003 Shimizu et al. ............ 428/64.1
6,746,629 B2  6/2004 Ozawa et al. ............... 252/589
6,836,383 B1 * 12/2004 Ozawa et al. ............... 359/885

FOREIGN PATENT DOCUMENTS

JP    2000-265077    9/2000
JP    2001-166131    6/2001

\* cited by examiner

*Primary Examiner*—Shean C Wu
(74) *Attorney, Agent, or Firm*—Fitzpatrick, Cella, Harper & Scinto

(57) ABSTRACT

A filter of an electronic display device provides a clear image, the filter comprising an squarylium compound represent by formula (II):

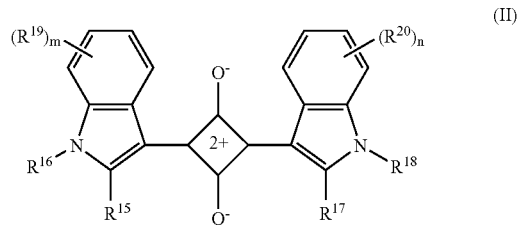

wherein $R^{15}$ and $R^{17}$ independently represent a hydrogen atom, a halogen atom, substituted or unsubstituted alkyl group, a substituted or unsubstituted alkoxyl group, a substituted or unsubstituted aralkyl group, a substituted or unsubstituted aryl group, a nitro group, a cyano group, a hydroxyl group, a substituted or unsubstituted amino group, or a substituted or unsubstituted heterocyclic group;

$R^{16}$ and $R^{18}$ independently represent an alkoxyalkoxyl-substituted alkyl group;

$R^{19}$ and $R^{20}$ independently represent a halogen atom, a substituted or unsubstituted alkyl group, a substituted or unsubstituted alkoxyl group, a substituted or unsubstituted aralkyl group, a substituted or unsubstituted aryl group, a nitro group, a cyano group, a hydroxyl group, a substituted or unsubstituted amino group, or a substituted or unsubstituted heterocyclic group;

m represents an integer of 0 to 4, wherein, when m is 2 to 4, $R^{19}$ may be the same or different, respectively; and n represents an integer of 0 to 4, wherein, when n is 2 to 4, $R^{20}$ may be the same or different respectively.

3 Claims, No Drawings

FILTERS OF ELECTRONIC DISPLAYS

TECHNICAL FIELD

The present invention relates to filters of an electronic display device, capable of selectively blocking light with wavelengths that degrade color purity.

BACKGROUND ART

An electronic display device, ideally, displays a color image by a combination of three primary colors, i.e., red, blue, and green. In an actual display device, however, there has been a problem that since unwanted light other than light of the three primary colors (e.g., in a plasma display panel, light with a wavelength of 550 to 600 nm: neon emissions) is also involved in the image, the color purity of the image is degraded. In order to solve such a problem, a display device with a filter having a color correction function has been invented.

It has been known that a squarylium compound is used as a coloring agent for filters of electronic display devices. For example, Japanese Published Unexamined Patent Application No. 2001-192350 discloses a plasma display panel containing a squarylium compound represented by the following formula, etc.

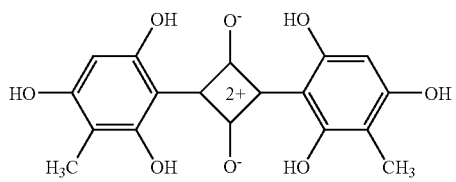

However, the above plasma display panel is not satisfactory in practical use because the light transmittance is insufficient in the wavelength range near 500 nm.

DISCLOSURE OF THE INVENTION

It is an object of the present invention to provide a filter of an electronic display device which selectively blocks light with wavelengths that degrade color purity and can provide a clear image.

The present invention provides the following [1] to [5].

[1] A filter of an electronic display device comprising a squarylium compound represented by general formula (I):

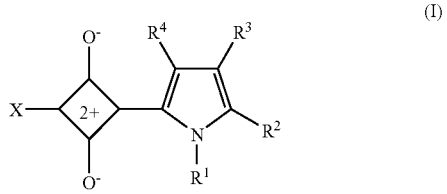

[wherein $R^1$ represents a hydrogen atom, a substituted or unsubstituted alkyl group, a substituted or unsubstituted aryl group, a substituted or unsubstituted aralkyl group, or a substituted or unsubstituted heterocyclic group; $R^2$, $R^3$ and $R^4$, which may be the same or different, each represent a hydrogen atom, a halogen atom, a substituted or unsubstituted alkyl group, a substituted or unsubstituted alkoxyl group, a substituted or unsubstituted aralkyl group, a substituted or unsubstituted aryl group, a nitro group, a cyano group, a hydroxyl group, a formyl group, a substituted or unsubstituted alkanoyl group, a substituted or unsubstituted alkoxycarbonyl group, a substituted or unsubstituted amino group, or a substituted or unsubstituted heterocyclic group; and X represents a group represented by formula (A):

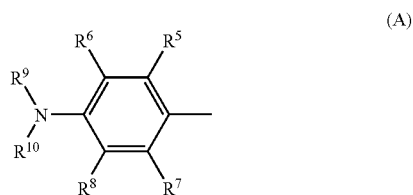

(wherein $R^5$, $R^6$, $R^7$ and $R^8$, which may be the same or different, each represent a hydrogen atom, a halogen atom, a substituted or unsubstituted alkyl group, a substituted or unsubstituted alkoxyl group, a substituted or unsubstituted aralkyl group, a substituted or unsubstituted aryl group, a nitro group, a cyano group, a hydroxyl group, or a substituted or unsubstituted heterocyclic group; and $R^9$ and $R^{10}$, which may be the same or different, each represent a hydrogen atom or a substituted or unsubstituted alkyl group, or $R^9$ and $R^{10}$, together with their adjacing nitrogen atom, form a substituted or unsubstituted heterocyclic group, alternatively, either $R^6$ and $R^9$ or $R^8$ and $R^{10}$, together with their adjacing N—C—C, form a substituted or unsubstituted heterocycle group), or a group represented by formula (B):

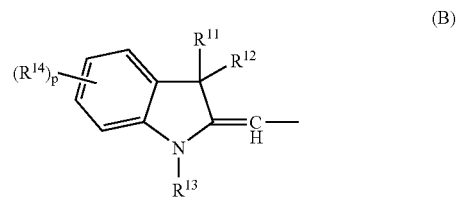

(wherein $R^{11}$ and $R^{12}$, which may be the same or different, each represent a hydrogen atom, a halogen atom, a substituted or unsubstituted alkyl group, a substituted or unsubstituted alkoxyl group, a substituted or unsubstituted aralkyl group, a substituted or unsubstituted aryl group, a nitro group, a cyano group, a hydroxyl group, or a substituted or unsubstituted heterocyclic group; $R^{13}$ represents a hydrogen atom, a substituted or unsubstituted alkyl group, a substituted or unsubstituted aryl group, a substituted or unsubstituted aralkyl group, or a substituted or unsubstituted heterocyclic group; $R^{14}$ represents a halogen atom, a substituted or unsubstituted alkyl group, a substituted or unsubstituted alkoxyl group, a substituted or unsubstituted aralkyl group, a substituted or unsubstituted aryl group, nitro group, a cyano group, hydroxyl group, a substituted or unsubstituted amino group, or a substituted or unsubstituted heterocyclic group; and p represents an integer of 0 to 4, wherein, when p is 2 to 4, each of $R^{14}$'s may be the same or different, respectively)].

[2] A filter of an electronic display device comprising a squarylium compound represented by general formula (II):

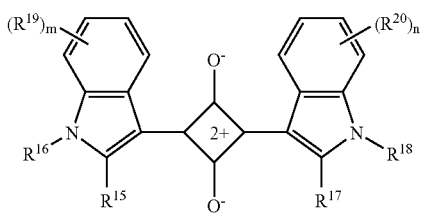

[wherein $R^{15}$ and $R^{17}$, which may be the same or different, each represents a hydrogen atom, a halogen atom, a substituted or unsubstituted alkyl group, a substituted or unsubstituted alkoxyl group, a substituted or unsubstituted aralkyl group, a substituted or unsubstituted aryl group, a nitro group, cyano group, a hydroxyl group, a substituted or unsubstituted amino group, or a substituted or unsubstituted heterocyclic group; $R^{16}$ and $R^{18}$, which may be the same or different, each represents a hydrogen atom, a substituted or unsubstituted alkyl group, a substituted or unsubstituted aryl group, a substituted or unsubstituted aralkyl group, or a substituted or unsubstituted heterocyclic group; $R^{19}$ and $R^{20}$, which may be the same or different, each represent a halogen atom, a substituted or unsubstituted alkyl group, a substituted or unsubstituted alkoxyl group, a substituted or unsubstituted aralkyl group, a substituted or unsubstituted aryl group, a nitro group, a cyano group, a hydroxyl group, a substituted or unsubstituted amino group, or a substituted or unsubstituted heterocyclic group; m represents an integer of 0 to 4, wherein, when m is 2 to 4, $R^{19}$'s may be the same or different, respectively; and n represents an integer of 0 to 4, wherein, when n is 2 to 4, $R^{20}$'s may be the same or different, respectively].

[3] The filter of an electronic display device according to [2], wherein $R^{16}$ and $R^{18}$, which may be the same or different, are each an alkoxyalkoxyl-substituted alkyl group.

[4] The filter of an electronic display device according to any one of [1] to [3], further comprising a binder.

[5] A squarylium compound represented by general formula (Ia):

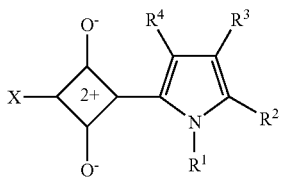

[wherein each of $R^1$, $R^2$, $R^3$ and $R^4$ is the same as that defined above; and X represents a group represented by formula (B):

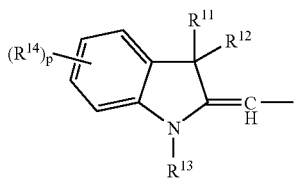

(wherein each of $R^{11}$, $R^{12}$, $R^{13}$, $R^{14}$ and p has the same meaning as defined above)].

Hereinafter, the compound represented by general formula (I) is referred to as Compound (I). The compounds with other formula numbers are also expressed similarly.

In the definition of each group in general formulae, examples of the alkyl group and alkyl moieties in the alkoxyl group, the alkanoyl group, and the alkoxycarbonyl group include linear or branched alkyl groups having 1 to 6 carbon atoms, and cyclic alkyl groups having 3 to 8 carbon atoms. Specific examples thereof include a methyl group, an ethyl group, a propyl group, an isopropyl group, a butyl group, an isobutyl group, a sec-butyl group, a tert-butyl group, a pentyl group, an isopentyl group, a 2-methylbutyl group, a tert-pentyl group, a hexyl group, a cyclopropyl group, a cyclobutyl group, a cyclopentyl group, a cyclohexyl group, a cycloheptyl group, a cyclooctyl group, etc.

Examples of the aryl group include a phenyl group, a naphthyl group, an anthryl group, etc.

Examples of the aralkyl group include aralkyl groups having 7 to 15 carbon atoms. Specific examples thereof include a benzyl group, a phenethyl group, a phenylpropyl group, a naphthylmethyl group, etc.

Examples of the halogen atom include a fluorine atom, a chlorine atom, a bromine atom, and an iodine atom.

Examples of the heterocycle in the heterocyclic group include aromatic heterocycles and aliphatic heterocycles.

Examples of the aromatic heterocycles include a 5- or 6-membered monocyclic aromatic heterocycles having at least one atom selected from the group consisting of nitrogen, oxygen, and sulfur atoms; and bicyclic or tricyclic condensed aromatic heterocycles, in which 3- to 8-membered rings are condensed, having at least one atom selected from the group consisting of nitrogen, oxygen, and sulfur atoms. More specific examples include a pyridine ring, a pyrazine ring, a pyrimidine ring, a pyridazine ring, a quinoline ring, an isoquinoline ring, a phthalazine ring, a quinazoline ring, a quinoxaline ring, a naphthyridine ring, a cinnoline ring, a pyrrole ring, a pyrazole ring, an imidazole ring, a triazole ring, a tetrazole ring, a thiophene ring, a furan ring, a thiazole ring, an oxazole ring, an indole ring, an isoindole ring, an indazole ring, a benzimidazole ring, a benzotriazole ring, a benzothiazole ring, a benzoxazole ring, a purine ring, a carbazole ring, etc.

Examples of the aliphatic heterocycle include a 5- or 6-membered monocyclic aliphatic heterocycles having at least one atom selected from the group consisting of nitrogen, oxygen, and sulfur atoms; and bicyclic or tricyclic condensed aliphatic heterocycles, in which 3- to 8-membered rings are condensed, having at least one atom selected from the group consisting of nitrogen, oxygen, and sulfur atoms. More specific examples include a pyrrolidine ring, a piperidine ring, a piperazine ring, a morpholine ring, a thiomorpholine ring, a homopiperidine ring, a homopiperazine ring, a tetrahydropyridine ring, a tetrahydroquinoline ring, a tetrahydroisoquinoline ring, a tetrahydrofuran ring, a tetrahydropyran ring, a dihydrobenzofuran ring, a tetrahydrocarbazole ring, etc.

Examples of the heterocycle formed by either $R^6$ and $R^9$ or $R^8$ and $R^{10}$ together with their adjacent N—C—C and the heterocycle in the heterocyclic group formed by $R^9$ and $R^{10}$ together with their adjacent nitrogen atom include 5- or 6-membered monocyclic heterocycles having at least one nitrogen atom, (wherein the monocyclic heterocycles may contain another nitrogen atom, an oxygen atom, or a sulfur atom); and bicyclic or tricyclic condensed heterocycles, in which 3- to 8-membered rings are condensed, having at least one nitrogen atom, (wherein the condensed heterocycle may contain another nitrogen atom, an oxygen atom, or a sulfur atom). Specific examples thereof include a pyrrolidine ring, a piperidine ring, a piperazine ring, a morpholine ring, a thiomorpholine ring, a homopiperidine ring, a homopiperazine ring, a tetrahydropyridine ring, a tetrahydroquinoline ring, a tetrahydroisoquinoline ring, a pyrrole ring, an imidazole ring, a pyrazole ring, an indole ring, an indoline ring, an isoindole ring, etc.

The substituent of the alkyl group, the alkoxyl group, the alkanoyl group, and the alkoxycarbonyl group is 1 to 3 substituent(s) which may be the same or different. Specific examples of the substituents include a hydroxyl group, a carboxyl group, a halogen atom, an alkoxyl group, an alkoxyalkoxyl group, etc. The halogen atom and the alkoxyl group have the same meanings as those defined above, respectively. Two alkoxy moieties in the alkoxyalkoxyl group have the same meaning as that defined above, respectively.

The substituent of the aralkyl group, the aryl group, the heterocyclic group, the heterocycle formed by either $R^6$ and $R^9$ or $R^8$ and $R^{10}$ together with their adjacent N—C—C, and the heterocycle in the heterocyclic group formed by $R^9$ and $R^{10}$ together with their adjacent nitrogen atom is 1 to 5 substituent(s) which may be the same or different. Specific examples of the substituents include a hydroxyl group, a carboxyl group, a halogen atom, an alkyl group, an alkoxyl group, a nitro group, a substituted or unsubstituted amino group, etc. The halogen atom, the alkyl group, and the alkoxyl group have the same meanings as those defined above, respectively.

The substituent of the amino group is one or two substituent(s) which may be the same or different, and specific examples of the substituents include an alkyl group, etc. The alkyl group has the same meaning as that defined above.

As Compound (II), compounds, wherein $R^{16}$ and $R^{18}$, which may be the same or different, are each an alkoxyalkoxyl-substituted alkyl group, are preferable.

Each of Compounds (I) and (Ia) may be produced by or according to a known method (e.g., WO01/44233). Compound (II) may be produced by or according to a known method [e.g., Dyes and Pigments, 49, 161 (2001)].

For example, Compound (Ia) may be produced as follows.
Reaction Formula (1-a)

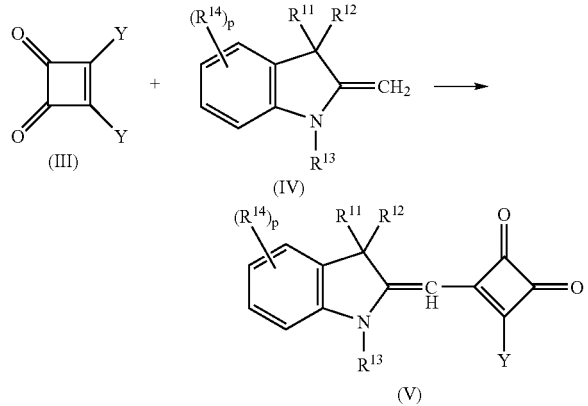

Reaction Formula (1-b)

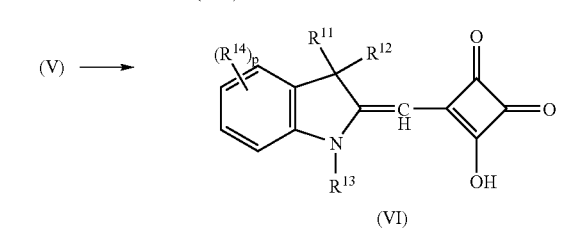

Reaction Formula (1-c)

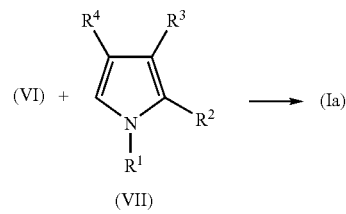

(In the formulae, each of $R^1$, $R^2$, $R^3$, $R^4$, $R^{11}$, $R^{12}$, $R^{13}$, $R^{14}$ and p is the same as that defined above, and Y is a halogen atom which is the same as that defined above or an alkoxyl group which is the same as that defined above.)

Reaction Formula (1-a)

Compound (V) is prepared by the reaction of Compound (III) and Compound (IV) in an amount of 1 to 2 molar times based on Compound (III) in a solvent, and as necessary, in the presence of a base, such as pyridine, at 0° C. to 100° C. for 0.5 to 10 hours.

Examples of solvents which may be used include alcohols, such as methanol, ethanol, propanol, butanol, etc.; and other solvents, such as chloroform, dichloromethane, 1,2-dichloromethane, ethyl acetate, diethyl ether, tetrahydrofuran, toluene, xylene, etc.

Reaction Formula (1-b)

Compound (VI) is prepared by treating Compound (V) in an acidic solvent at room temperature to 120° C. for 0.5 to 10 hours.

As the acidic solvent, for example, a mixed solvent of an inorganic acid such as hydrochloric acid sulfuric acid an organic acid etc., such as acetic acid trifluoroacetic acid, etc. (10 to 90 percent by volume) with tetrahydrofuran, dimethyl sulfoxide, N,N-dimethylformamide, water, etc, or the like is used.

Reaction Formula (1-c)

Compound (Ia) is prepared by the reaction of Compound (VI) and Compound (VII) in an amount of 1 to 2 molar times based on Compound (VI) in a solvent at 80° C. to 120° C. for 1 to 15 hours.

Examples of solvents which may be used include an alcohol solvent such as ethanol, propanol, isopropyl alcohol, butanol, octanol, etc.; and a mixed solvent of the alcohol solvent (50 percent by volume or more) with benzene, toluene, xylene, or the like.

Preferred examples of Compounds (I) and (II) will be illustrated below. In the structural formulae for Compounds 1 to 4, Me, Et, and Bu represent methyl, ethyl, and butyl, respectively.

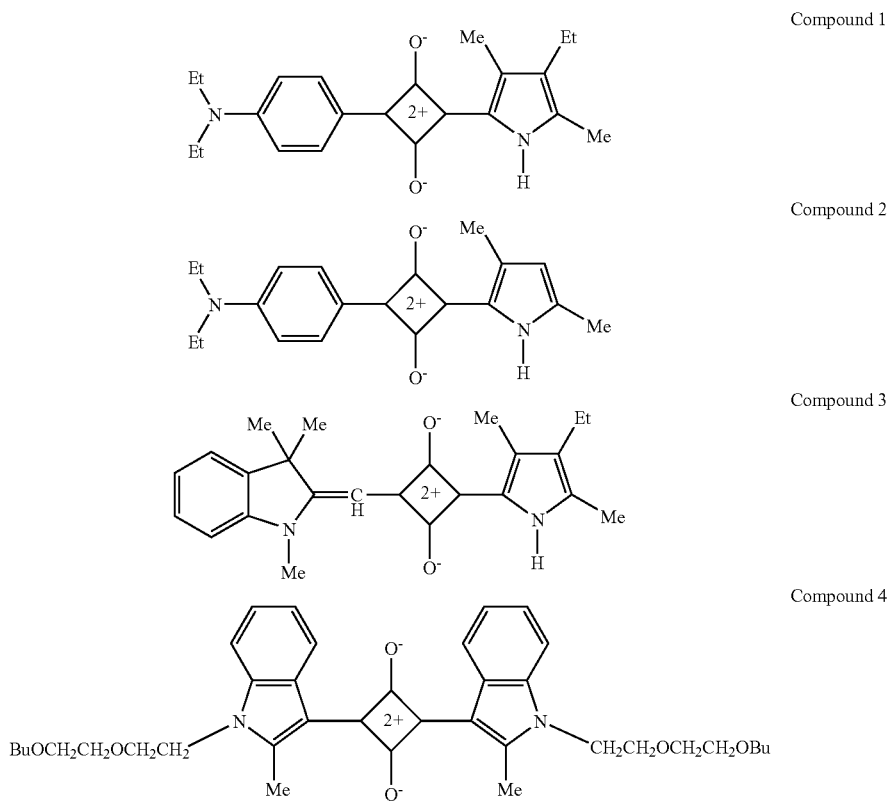

Compound 1

Compound 2

Compound 3

Compound 4

The filter of an electronic display device of the present invention will now be described.

Examples of the electronic display include liquid crystal displays, plasma displays, organic electroluminescent displays and the like. Among these displays, plasma displays are preferred.

Compound (I) or (II) used for the filter of electronic display devices of the present invention exhibits an absorption maximum preferably in the absorption range of 550 to 610 nm, and more preferably in the absorption range of 570 to 610 nm, in a chloroform solution. In Compound (I) or (II) used for the filter of the electronic display device of the present invention, the logarithm of the molar extinction coefficient is preferably 4.5 or more, and more preferably 4.8 or more.

In the filter of electronic display devices of the present invention, the absorption maximum is preferably in the absorption range of 550 to 610 nm, and more preferably in the absorption range of 570 to 610 nm.

In order to fabricate the filter of the electronic display devices of the present invention, preferably, a coating liquid of Compound (I) or (II) is applied to a transparent substrate and an organic solvent is then removed by evaporation. As necessary, another transparent substrate may be bonded to the coated substrate.

The coating liquid may be prepared by dissolving a binder in a solution of an organic solvent containing Compound (I) or (II).

Examples of organic solvents include ethers such as dimethoxyethane, methoxyethoxyethane, tetrahydrofuran, and dioxane, etc.; ketones such as acetone, methylethylketone, methylisobutylketone, and cyclohexanone, etc.; and aromatic hydrocarbons such as benzene, toluene, xylene, and monochlorobenzene. Preferably, the organic solvent is used in an amount of 10 to 3,000 times (by weight) based on Compound (I) or (II).

Examples of binders include polyester resins, polycarbonate resins, polyacrylic resins, polystyrene resins, poly(vinyl chloride) resins, poly(vinyl acetate) resins, etc. Preferably, the binder is used in an amount of 10 to 500 times (by weight) based on Compound (I) or (II).

As the transparent substrate, any transparent resin or glass with low absorptivity and low scattering coefficient may be used. Examples of resins include polyester resins, polycarbonate resins, polyacrylic resins, polystyrene resins, poly(vinyl chloride) resins, poly(vinyl acetate) resins, etc.

As the method for applying the coating liquid of Compound (I) or (II) to the transparent substrate, a known coating method such as a bar-coating method, a spray method, a roll-coating method, or a dipping method may be used (e.g., U.S. Pat. No. 2,681,294).

Compound (I) or (II) is highly soluble in an organic solvent and is suitable for the method of fabricating the filter of the electronic display devices using the above-mentioned coating liquid.

In order to fabricate the filter of the electronic display device of the present invention, another method may be employed in which Compound (I) or (II) is directly dissolved or dispersed in the resin constituting a transparent substrate and then formed into a film. As necessary, another transparent substrate may be bonded to one or each side of the coated substrate.

In the film formed using Compound (I) or (II), preferably, the absorption width with a transmittance of 50% in the vicinity of the absorption maximum wavelength (i.e., the difference between the maximum absorption wavelength and the minimum absorption wavelength exhibiting a transmittance of 50% or less in the vicinity of the absorption maximum wavelength) is 80 nm or less. Preferably, the film formed using Compound (I) or (II) has sufficient transmittance in the range of 400 to 500 nm. For example, in the film in which the absorption maximum is in the absorption range of 550 to 610 nm, the transmittance at 500 nm is preferably 80% or more.

The filter of an electronic display devices of the present invention selectively blocks light with wavelengths that degrade color purity while maintaining a bright view, is excellent in color correction function, and can provide a clear image with excellent color can be displayed.

The filters of an electronic display device of the present invention may be used for Braun tubes, fluorescent display tubes, electroluminescence panels, light-emitting diodes, plasma display panels, heat-generating electric lamps, laser displays, liquid crystal displays, electrochromic displays, or the like.

BEST MODE FOR CARRYING OUT THE INVENTION

The present invention will be described in more detail based on examples and reference examples below.

REFERENCE EXAMPLE 1

Process for Producing Compound 1

A dichloromethane solution (32 mL) in which 2.8 g of squaric acid dichloride was dissolved was cooled to 0° C. to 5° C., and 1.5 g of pyridine was added thereto. A dichloromethane solution (20 mL) in which 5.3 g of N,N-diethylaniline was dissolved was then dripped into the mixture for over 30 minutes. The mixture was heated to room temperature and stirred for 4 hours. An ocherous solid was collected from the mixture by silica gel chromatography using dichloromethane as a developing solvent. Acetic acid (4 mL) and water (4 mL) were added to the ocherous solid and a reaction was carried out at 110° C. for 2 hours. The reaction solution was then cooled to 0° C. to 5° C. Water (50 mL) was added to the reaction solution, and the precipitated yellow solid was collected by filtration. 2,4-Dimethyl-3-ethylpyrrole (0.9 g), butanol (22 mL), and toluene (11 mL) were added to the yellow solid, and a reaction was carried out at 110° C. for 2 hours. The reaction solution was then cooled to 0° C. to 5° C. Methanol (40 mL) was added to the reaction solution, and the precipitate was collected by filtration. Compound 1 (0.2 g) was thereby prepared.

$^1$H-NMR $\delta$(CDCl$_3$) ppm: 1.09 (3H, t, J=7.6 Hz), 1.23 (3H, t, J=7.3 Hz), 2.36 (3H,s), 2.41 (2H, q, J=7.6 Hz), 2.62 (3H, s), 3.48 (2H, q, J=7.3 Hz), 6.71 (2H, d, J=9.3 Hz), 8.24 (2H, d, J=9.3 Hz), 10.3 (1H, brs).

REFERENCE EXAMPLE 2

Process for Producing Compound 2

Compound 2 (0.5 g) was prepared as in Example 1 except that 2,4-dimethylpyrrole (0.7 g) was used instead of 2,4-dimethyl-3-ethylpyrrole.

$^1$H-NMR $\delta$(CDCl$_3$) ppm: 1.26 (6H, t, J=7.2 Hz), 2.40 (3H, s), 2.66 (3H, s), 3.50 (4H, q, J=7.2 Hz), 6.17 (1H, m), 6.72 (2H, d, J=9.3 Hz), 8.26 (2H, d, J=8.5 Hz), 10.2 (1H, brs).

EXAMPLE 1

Process for Producing Compound 3

A mixture of 5.3 g of squaric acid dimethyl ester, 6.4 g of 1,3,3-trimethyl-2-methyleneindoline, and 50 mL of ethanol was refluxed while being heated for 1 hour, and the precipitated solid was collected by filtration. The solid was placed into a mixed solvent of 50 mL of N,N-dimethylformamide with 3 mL of 1 mol/L hydrochloric acid, and allowed to stand at 80° C. for 2 hours. A methanol aqueous solution (50 percent by volume) (50 mL) was added to the mixture and insolubles were collected by filtration. The insolubles and 4.1 g of 2,4-dimethyl-3-ethylpyrrole were added into a mixed solvent of 65 mL of butanol with 33 mL of toluene, and a reaction was carried out at 110° C. for 7 hours, followed by cooling. Methanol (261 mL) was added to the mixture, and the precipitate was collected by filtration. Compound 3 (3.3 g) was thereby prepared.

1H-NMR $\delta$(CDCl$_3$) ppm: 1.08 (3H, t, J=7.6 Hz), 1.63 (6H, s), 1.77 (3H, s), 2.32 (3H, s), 2.43 (2H, q, J=7.6 Hz), 2.59 (3H, s), 3.61(3H, s), 5.94 (1H, s), 7.04 (1H, d, J=7.8 Hz), 7.17-7.21 (1H, m), 7.32-7.38 (2H, m), 9.95 (1H, brs).

REFERENCE EXAMPLE 3

Process for producing Compound 4

Squaric acid (20.0 g) and 1-butoxyethoxyethylindole (100 g) were added into a mixed solvent of 170 mL of butanol with 170 mL of toluene, and a reaction was carried out at 100° C. to 110° C. for 5 hours. The reaction solution was then cooled to 70° C., and 220 mL of methanol was added thereto. The mixture was cooled to 15° C., and the precipitate was collected by filtration. Compound 4 (33.3 g) was thereby prepared.

$^1$H-NMR $\delta$(CDCl$_3$) ppm: 0.89 (6H, t, J=7.3 Hz), 1.27-1.36 (4H, m), 1.47-1.54 (4H, m), 3.34-3.48 (10H, m), 3.51-3.54 (4H, m), 3.85 (4H, t, J=5.6 Hz), 4.36 (4H, t, J=5.6 Hz), 7.23-7.36 (6H, m), 9.21 (2H, d, J=7.8 Hz).

EXAMPLE 2

With respect to each of Compounds 1 to 4, the absorption maximum wavelength ($\lambda$max) and the logarithm (log$\epsilon$) of the molar extinction coefficient in a chloroform solution were measured (800 to 300 nm). The results thereof are shown in Table 1.

TABLE 1

Spectral characteristics of squarylium compounds

| Compound | Spectral characteristics (Chloroform solution) | |
| --- | --- | --- |
| | $\lambda$max (nm) | log$\epsilon$ |
| 1 | 593.0 | 5.1 |
| 2 | 594.0 | 5.3 |
| 3 | 601.5 | 5.4 |
| 4 | 580.0 | 5.2 |

EXAMPLE 3

A dimethoxyethane solution of Compound 1 (0.5 percent ethylpyrrole by weight) and a dimethoxyethane solution of polyester resin (VYLON 200 manufactured by Toyobo Co., Ltd.) (20 percent by weight) were mixed ate a ratio of 7:2, and the resultant mixture was applied onto a glass substrate by a bar coater, followed by drying. A coating film was thereby formed. The transmittance curve of the resultant film was measured (800 to 300 nm), and the absorption maximum wavelength, the absorption width with a transmittance of 50%, and the transmittance at 500 nm in the film were determined. The results thereof are shown in Table 2.

EXAMPLE 4

A dimethoxyethane solution of Compound 2 (0.1 percent by weight) and a dimethoxyethane solution of polyester resin (VYLON 200 manufactured by Toyobo Co., Ltd.) (20 percent by weight) were mixed at a ratio of 7:2, and the resultant mixture was applied onto a glass substrate by a bar coater, followed by drying. A coating film was thereby formed. The transmittance curve of the resultant film was measured (800 to 300 nm), and the absorption maximum wavelength, the absorption width with a transmittance of 50%, and the transmittance at 500 nm in the film were determined. The results thereof are shown in Table 2.

EXAMPLE 5

A dimethoxyethane solution of Compound 3 (0.5 percent by weight) and a dimethoxyethane solution of polyester resin (VYLON 200 manufactured by Toyobo Co., Ltd.) (20 percent by weight) were mixed at a ratio of 7:2, and the resultant mixture was applied onto a glass substrate by a bar coater, followed by drying. A coating film was thereby formed. The transmittance curve of the resultant film was measured (800 to 300 nm), and the absorption maximum wavelength, the absorption width with a transmittance of 50%, and the transmittance at 500 nm in the film were determined. The results thereof are shown in Table 2.

EXAMPLE 6

A tetrahydrofuran solution of Compound 4 (0.6 percent by weight) and a dimethoxyethane solution of polyester resin (VYLON 200 manufactured by Toyobo Co., Ltd.) (20 percent by weight) were mixed at a ratio of 7:2, and the resultant mixture was applied onto a glass substrate by a bar coater, followed by drying. A coating film was thereby formed. The transmittance curve of the resultant film was measured (800 to 300 nm), and the absorption maximum wavelength, the absorption width with a transmittance of 50%, and the transmittance at 500 nm in the film were determined. The results thereof are shown in Table 2.

TABLE 2

Absorption maximum wavelength, absorption width with transmittance of 50%, and transmittance at 500 nm in squarylium compound films

| | Absorption maximum wavelength | Absorption width with transmittance of 50% | Transmittance at 500 nm |
|---|---|---|---|
| Compound 1 | 600.5 nm | 50 nm | 90% or more |
| Compound 2 | 601.0 nm | 53 nm | 95% or more |
| Compound 3 | 609.5 nm | 56 nm | 95% or more |
| Compound 4 | 586.0 nm | 52 nm | 95% or more |

As is evident from the results described above, the filter of electronic display devices of the present invention are capable of selectively blocking light with wavelengths that degrade color purity, and clear images can be provided.

INDUSTRIAL APPLICABILITY

In accordance with the present invention, a filter of an electronic display device, which selectively blocks light with wavelengths that degrade color purity and can provide a clear image, can be provided.

The invention claimed is:

1. A filter of an electronic display device, said filter comprising a squarylium compound represented by formula (II):

$$(II)$$

wherein
$R^{15}$ and $R^{17}$ independently represent a hydrogen atom, a halogen atom, a substituted or unsubstituted alkyl group, a substituted or unsubstituted alkoxyl group, a substituted or unsubstituted aralkyl group, a substituted or unsubstituted aryl group, a nitro group, a cyano group, a hydroxyl group, a substituted or unsubstituted amino group, or a substituted or unsubstituted heterocyclic group;

$R^{16}$ and $R^{18}$ independently represent an alkoxyalkoxyl-substituted alkyl group;

$R^{19}$ and $R^{20}$ independently represent a halogen atom, a substituted or unsubstituted alkyl group, a substituted or unsubstituted alkoxyl group, a substituted or unsubstituted aralkyl group, a substituted or unsubstituted aryl group, a nitro group, a cyano group, a hydroxyl group, a substituted or unsubstituted amino group, or a substituted or unsubstituted heterocyclic group;

m represents an integer of 0 to 4, wherein, when m is 2 to 4, $R^{19}$'s may be the same or different, respectively; and n represents an integer of 0 to 4, wherein, when n is 2 to 4, $R^{20}$'s may be the same or different, respectively.

2. The filter according to claim 1, further comprising a binder.

3. The filter according to claims 1 or 2, wherein
the alkyl group and alky moieties in the alkoxyl, alkanoyl alkoxylcarbonyl groups is linear or branched $C_1$-$C_6$ alkyl, or $C_3$-$C_8$ cyclic alkyl,
the aralkyl group is $C_7$-$C_{15}$,
the heterocycle in the heterocyclic group is (i) a 5- or 6-membered monocyclic aromatic heterocycle having at least one atom selected from the group consisting of nitrogen, oxygen and sulfur, or a bicyclic or tricyclic condensed aromatic heterocycle in which 3- to 8-membered rings are condensed having at least one atom selected from the group consisting of nitrogen, oxygen or sulfur, or (ii) a 5- or 6-membered monocyclic aliphatic heterocycle having at least one atom selected from the group consisting of nitrogen, oxygen and sulfur, or a bicyclic or tricyclic condensed aliphatic heterocycle in which 3- to 8-membered rings are condensed, having at least one atom selected from the group consisting of nitrogen, oxygen and sulfur, substituents of the alkyl group, the alkoxyl group, the alkanoyl group and the alkoxycarbonyl group are 1-3 substituents independently selected from the group consisting of hydroxyl, carboxyl, halogen, alkoxyl and alkoxyalkoxyl, and substituents of the aralkyl group, the aryl group and the heterocyclic group are 1 to 5 substituents independently selected from the group consisting of hydroxyl, carboxyl, halogen, alkyl, alkoxyl, nitro, and amino optionally substituted with one or two alkyl groups.

* * * * *

UNITED STATES PATENT AND TRADEMARK OFFICE
CERTIFICATE OF CORRECTION

PATENT NO. : 7,242,542 B2
APPLICATION NO. : 10/516749
DATED : July 10, 2007
INVENTOR(S) : Ikuo Shimizu et al.

It is certified that error appears in the above-identified patent and that said Letters Patent is hereby corrected as shown below:

ON THE TITLE PAGE Item [57] [ABSTRACT]:

Line 3, "resent" should read --resented--.

COLUMN 2:

Line 30, "adjacing" should read --adjacent--; and
Line 33, "adjacing" should read --adjacent--.

COLUMN 3:

Line 18, "cyano group," should read --a cyano group,--.

COLUMN 6:

Line 44, "hydrochloric acid sulfuric acid" should read --hydrochloric acid, sulfuric acid,--; and
Line 45, "acetic acid" should read --acetic acid,--.

COLUMN 9:

Line 11, "devices" should read --device--; and
Line 15, "can be displayed." should be deleted.

COLUMN 10:

Line 19, "1H-NMR" should read --'H-NMR--; and
Line 67, "ethylpyrrole" should be deleted.

COLUMN 11:

Line 2, "ate" should read --at--; and
Line 66, "filter" should read --filters--.

UNITED STATES PATENT AND TRADEMARK OFFICE
CERTIFICATE OF CORRECTION

PATENT NO. : 7,242,542 B2
APPLICATION NO. : 10/516749
DATED : July 10, 2007
INVENTOR(S) : Ikuo Shimizu et al.

It is certified that error appears in the above-identified patent and that said Letters Patent is hereby corrected as shown below:

COLUMN 12:

Line 51, "alky" should read --alkyl--.

Signed and Sealed this

Thirteenth Day of November, 2007

JON W. DUDAS
*Director of the United States Patent and Trademark Office*